US012655574B2

(12) United States Patent
Byoun et al.

(10) Patent No.: US 12,655,574 B2
(45) Date of Patent: Jun. 16, 2026

(54) LAUNDRY DRYER AND METHOD FOR CONTROLLING LAUNDRY DRYER

(71) Applicant: LG Electronics Inc., Seoul (KR)

(72) Inventors: Youngmin Byoun, Seoul (KR); Daehyun Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 478 days.

(21) Appl. No.: 17/909,258

(22) PCT Filed: Feb. 25, 2021

(86) PCT No.: PCT/KR2021/002370
§ 371 (c)(1),
(2) Date: Sep. 2, 2022

(87) PCT Pub. No.: WO2021/177656
PCT Pub. Date: Sep. 10, 2021

(65) Prior Publication Data
US 2023/0089461 A1       Mar. 23, 2023

(30) Foreign Application Priority Data
Mar. 4, 2020     (KR) ........................ 10-2020-0026954

(51) Int. Cl.
D06F 58/45          (2020.01)
A61L 2/07          (2006.01)
(Continued)

(52) U.S. Cl.
CPC ................ D06F 58/45 (2020.02); A61L 2/07 (2013.01); D06F 58/02 (2013.01); D06F 58/206 (2013.01); D06F 58/24 (2013.01)

(58) Field of Classification Search
None
See application file for complete search history.

(56) References Cited

U.S. PATENT DOCUMENTS

2006/0005581 A1* 1/2006 Banba ................... D06F 35/006
                                                              68/5 R
2008/0092928 A1* 4/2008 Wong ..................... D06F 17/12
                                                              134/30
(Continued)

FOREIGN PATENT DOCUMENTS

CN          101302708 A     11/2008
CN          102037176 A     4/2011
(Continued)

OTHER PUBLICATIONS

Sobieski, How to Troubleshoot an Overheating Compressor, Aug. 31, 2015, Sobieski, https://www.sobieskiinc.com/blog/how-troubleshoot-overheating-compressor/#:~:text=lf%20the%20compressor%20is%20short,faulty%20capacitor%20or%20metering%20device. (Year: 2015).*

(Continued)

*Primary Examiner* — Omair Chaudhri
(74) *Attorney, Agent, or Firm* — Fish & Richardson P.C.

(57) ABSTRACT

A method for controlling a laundry dryer includes a steam supplying step for supplying steam to a heat exchange unit, a cleaning step for controlling a cleaning unit after the steam supplying step to spray cleaning water to the heat exchange unit according to preset spraying criteria, and a drying step for drying the heat exchange unit after the cleaning step. The method is performed for eliminating and sterilizing foreign substances, microorganisms, and the like in the heat exchange unit.

10 Claims, 10 Drawing Sheets

(51) Int. Cl.
  D06F 58/02    (2006.01)
  D06F 58/20    (2006.01)
  D06F 58/24    (2006.01)

(56)            References Cited

U.S. PATENT DOCUMENTS

| | | | |
|---|---|---|---|
| 2009/0241269 A1* | 10/2009 | Yoo | D06F 73/02 |
| | | | 8/149.3 |
| 2011/0277334 A1* | 11/2011 | Lee | D06F 58/206 |
| | | | 34/73 |
| 2013/0232813 A1* | 9/2013 | Heo | F26B 21/086 |
| | | | 34/515 |
| 2017/0191209 A1* | 7/2017 | Kim | D06F 37/04 |
| 2018/0030643 A1* | 2/2018 | Kim | D06F 58/206 |
| 2019/0024299 A1* | 1/2019 | Ryu | D06F 58/22 |
| 2021/0198836 A1* | 7/2021 | Kitayama | D06F 59/02 |
| 2022/0042230 A1* | 2/2022 | Kim | D06F 58/20 |

FOREIGN PATENT DOCUMENTS

| | | | | |
|---|---|---|---|---|
| CN | 107663760 A | 2/2018 | | |
| CN | 107687079 A | 2/2018 | | |
| EP | 1275767 A1 * | 1/2003 | ............. | D06F 35/00 |
| EP | 2325375 A1 * | 5/2011 | ........... | D06F 35/008 |
| EP | 2341183 A1 | 7/2011 | | |
| EP | 2628844 A1 * | 8/2013 | ........... | D06F 58/206 |
| JP | 2008-006068 | 1/2008 | | |
| JP | 2013202159 | 10/2013 | | |
| JP | 5942098 | 6/2016 | | |
| KR | 10-2012-0005266 A | 1/2012 | | |
| KR | 20120110498 | 10/2012 | | |
| KR | 20170028037 | 3/2017 | | |
| KR | 20180013535 | 2/2018 | | |
| KR | 10-2019-0128484 A | 11/2019 | | |
| WO | WO-2016108793 A1 * | 7/2016 | .......... | D06F 58/206 |
| WO | WO 2018/024228 | 2/2018 | | |
| WO | WO-2018024228 A1 * | 2/2018 | ............. | D06F 58/10 |

OTHER PUBLICATIONS

Pacific Heating and Cooling, Common Compressor Problems & Solutions, Dec. 27, 2018, Pacific Heating and Cooling, https://www.pacificheatingcooling.com/2018/12/27/common-compressor-problems-solutions/ (Year: 2018).*

Extended European Search Report in European Appln. No. 21765341. 9, mailed on Feb. 20, 2024, 9 pages.

International Search Report and Written Opinion in International Appln. No. PCT/KR2021/002370, dated Jun. 22, 2021, 13 pages (with English translation).

Notice of Allowance in Korean Appln. No. 10-2020-0026954, mailed on May 7, 2025, 3 pages (with English translation).

Office Action in Chinese Appln. No. 202180018784.9, mailed on Apr. 30, 2025, 10 pages (with English translation).

Office Action in Korean Appln. No. 10-2020-0026954, mailed on Dec. 12, 2024, 4 pages.

* cited by examiner

FIG. 4

|  |  |
|---|---|
| ———————— | duct |
| — — — — — | comp |
| ———————— | Drying Fan |
| —·—·—·— | Pump RPM10 |
| ———————— | Com Hz |

FIG. 9

| Strain | Staphylococcus aureus | Escherichia coli | Pseudomonas aeruginosa | Klebsiella pneumoniae |
|---|---|---|---|---|
| Sterilization condition | 60 °C 30 Minutes 70 °C 10 Minutes | 60 °C 10 Minutes | 55 °C 30 Minutes | Klebsiella pneumoniae 50 °C 20 Minutes |

LAUNDRY DRYER AND METHOD FOR CONTROLLING LAUNDRY DRYER

CROSS-REFERENCE TO RELATED APPLICATIONS

This application is a National Stage application under 35 U.S.C. § 371 of International Application No. PCT/KR2021/002370, filed on Feb. 25, 2021, which claims the benefit of Korean Application No. 10-2020-0026954, filed on Mar. 4, 2020. The disclosures of the prior applications are incorporated by reference in their entirety.

TECHNICAL FIELD

The present disclosure relates to a laundry dryer and a method for controlling the laundry dryer, and more particularly, to a laundry dryer and a method for controlling the laundry dryer for generating high-temperature steam via a steam generator and controlling rotation of a drum and rotation of a fan independently.

BACKGROUND

A laundry treating apparatus may perform a drying cycle for removing moisture from laundry. For example, a laundry treating apparatus may shorten a drying time of the laundry and perform sterilization and disinfection of the laundry by supplying hot air to a drum for accommodating therein the laundry to dry the laundry.

In some cases, the laundry treating apparatus for performing the drying cycle also includes a laundry treating apparatus for supplying steam to the laundry in order to remove wrinkles of the laundry, improve a drying efficiency, or perform the sterilization or the like.

In some cases, a condensing dryer may be equipped with a heat pump system.

In some cases, the condensing dryer may have contamination issues caused by condensate. Specifically, in an evaporator, humidity of air that has dried an object-to-be-dried while passing through the drum decreases and the condensate is generated. The condensate may contain contaminants or bacteria contained in the drum and the object-to-be-dried, and the bacteria may contaminate at least one of the evaporator, a water container, washing device, and a pump through which the condensate passes.

When a heat exchanger is contaminated by the bacteria or the like, air circulating in a flow path may have a bad smell caused by the bacteria, and such smell may permeate the object-to-be-dried and deteriorate a drying quality. In addition, a large amount of condensate generated in the heat exchanger provides a favorable environment for reproduction of the bacteria, so that the contamination of the heat exchanger by the bacteria may be accelerated.

In the heat exchanger of the dryer as described above, the contamination by the bacteria or the contaminants occurred during a heat exchange process may be resolved by a user washing the heat exchanger by himself/herself. However, it may be difficult to wash the heat exchanger disposed inside the dryer because of a structure of the dryer, so that there is a limit of causing inconvenience to the user.

That is, the dryer may have the problem of the contamination by the bacteria occurred during the heat exchange process, but there is no specific method to prevent or resolve the contamination by the bacteria. Therefore, there is a limit that a performance, a hygiene, the drying quality, and user convenience and satisfaction of the dryer are not able to be satisfied.

SUMMARY

The present disclosure describes a laundry dryer and a method for controlling the laundry dryer capable of washing a heat exchanger in the dryer.

According to one aspect of the subject matter described in this application, a laundry dryer includes a cabinet that defines an outer appearance of the laundry dryer, a drum rotatably located in the cabinet and configured to accommodate an object to be dried therein, a duct assembly configured to guide air discharged from the drum and to supply the air to the drum, a circulation fan configured to cause the air to move along the duct assembly, a heat exchange assembly disposed in the duct assembly and configured to exchange heat with the air in the duct assembly, a compressor configured to compress refrigerant to enable heat exchange between the refrigerant and the air in the duct assembly, a steam supply configured to generate steam and to supply the steam into the drum, a washing device configured to spray washing water toward a surface of the heat exchange assembly, a sensor configured to sense a temperature of the heat exchange assembly, and a controller configured to control the drum, the circulation fan, the compressor, the steam supply, and the washing device. The controller is configured to perform washing and sterilization operations by operating the steam supply and then driving the compressor to thereby wash and sterilize the heat exchange assembly.

Implementations according to this aspect can include one or more of the following features. For example, the controller can be configured to, based on operating the steam supply, drive the circulation fan to thereby cause the steam to move toward the heat exchange assembly. In some examples, the controller can be configured to rotate the drum based on operating the steam supply. In some implementations, the controller can be configured to (i) control the steam supply to spray steam for a preset spray time, (ii) then control the steam supply to stop spraying steam for a preset pause time, and (ii) then control the steam supply to respray steam for the preset spray time. In some examples, the controller can be configured to rotate the circulation fan at a preset first circulation speed.

In some implementations, the washing device can include a washing water sprayer configured to spray the washing water to the heat exchange assembly, a drain pump configured to transfer condensate water stored in the cabinet, and a control valve configured to distribute the condensate water transferred by the drain pump toward the washing water sprayer, where the controller can be configured to, after terminating supply of the steam to the drum, control the washing device to spray the washing water to the heat exchange assembly based on a preset spray standard.

In some implementations, the controller can be configured to drive the compressor at a preset first compression frequency based on starting an operation of the washing device. In some examples, the controller can be configured to, after terminating the operation of the washing device, accelerate the compressor and drive the compressor at a preset second compression frequency. In some examples, the controller can be configured to, after terminating the operation of the washing device, rotate the circulation fan at a preset second circulation speed. In some examples, the controller can be configured to, after terminating supply of the steam to the drum, operate the drain pump for a washing time. In some implementations, the controller can be configured to perform the washing and sterilization operations without the object in the drum.

According to another aspect, a method for controlling a laundry dryer, which includes a heat exchange assembly and a washing device configured to wash the heat exchange assembly, includes supplying steam to the heat exchange assembly, after supplying the steam to the heat exchange assembly, spraying washing water to the heat exchange assembly by controlling the washing device, drying the heat exchange assembly after spraying the washing water to the heat exchange assembly, and blowing air toward the heat exchange assembly to thereby sterilize the heat exchange assembly by heating the heat exchange assembly based on a thermal equilibrium between the air and the heat exchange assembly.

Implementations according to this aspect can include one or more of the following features. For example, supplying the steam can include operating a steam supply to supply the steam to the heat exchange assembly, and rotating a circulation fan at a preset first circulation speed. In some examples, spraying the washing water can include spraying the washing water to the heat exchange assembly based on a preset spray standard.

In some examples, spraying the washing water can further include driving a compressor at a preset first compression frequency. In some examples, spraying the washing water can further include driving a drain pump for a preset washing time. In some implementations, drying the heat exchange assembly can include driving the compressor at a preset second compression frequency.

In some implementations, blowing the air includes stopping driving of a compressor to thereby sterilize an evaporator by heating the evaporator based on a thermal equilibrium between the air and the evaporator. In some examples, supplying the steam can include supplying water to the steam supply, heating the water by applying power to the steam supply to thereby generate steam, and spraying the steam generated from the steam supply. In some instances, spraying the steam can include spraying steam for a preset spray time, then stopping spraying steam for a preset pause time, and then respraying steam for the preset spray time.

In some implementations, the heat exchanger can be sterilized by controlling the surface temperature of the heat exchanger to be the temperature equal to or higher than the reference temperature at which the sterilization is performed.

In some implementations, as the surface temperature of the heat exchanger is increased to the temperature equal to or higher than the reference temperature at which the sterilization is performed via the driving control of the compressor, the heat exchanger can be sterilized simply without a separate component/means for the sterilization.

In some implementations, as the steam is supplied toward the heat exchanger in the steam supply step, the surface tension and the viscosity of the foreign substances and the microorganisms attached to the surface of the heat exchanger are reduced, so that the foreign substances and the microorganisms are easily removed from the heat exchanger.

BRIEF DESCRIPTION OF DRAWINGS

FIG. 4 is a block diagram illustrating an example of a control configuration of the laundry dryer.

FIG. 9 is a diagram illustrating an example of sterilization conditions according to a method for controlling a laundry dryer.

DETAILED DESCRIPTION

Hereinafter, one or more implementations of the present disclosure will be described in detail with reference to the accompanying drawings.

Figure 1:
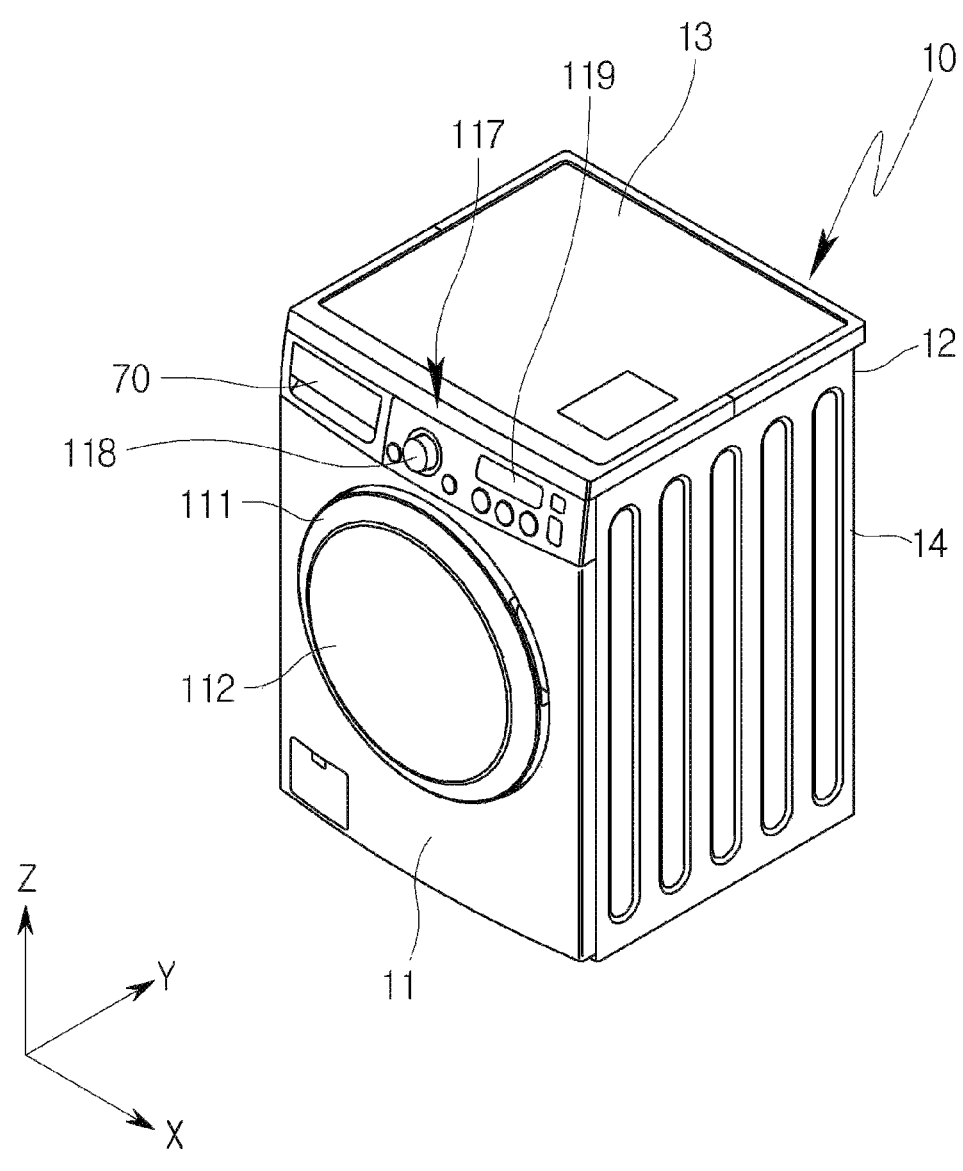
FIG. 1 is a view for illustrating an outer appearance of an example of a laundry dryer.
Figure 2:
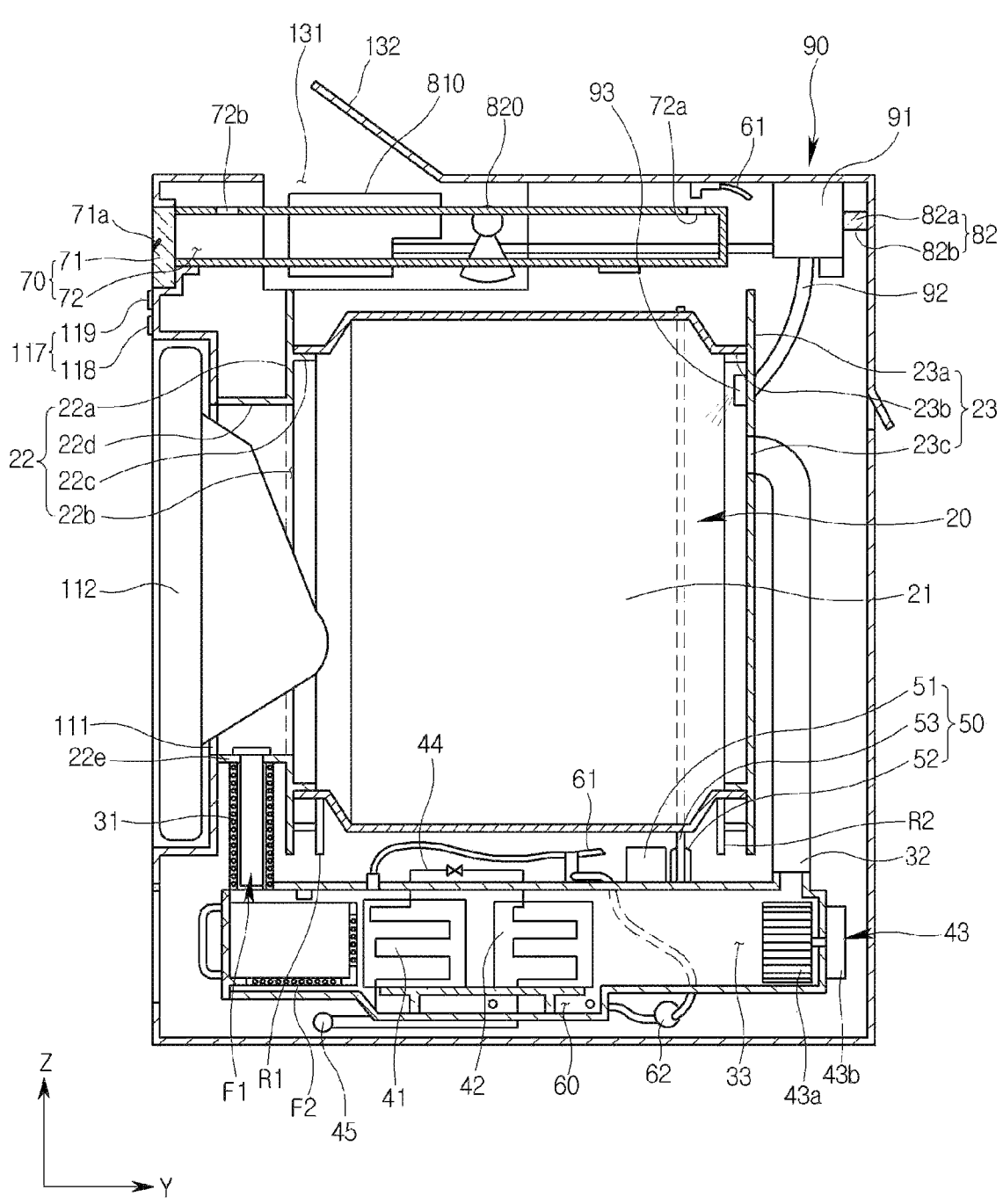
FIG. 2 is a cross-sectional view illustrating an example of an internal structure of the laundry dryer.

FIG. 1 is a view for illustrating an outer appearance of an example of a laundry dryer, and FIG. 2 is a cross-sectional view for illustrating an internal structure of a laundry dryer.

In some implementations, as shown in FIGS. 1 and 2, a cabinet 10 defines an outer body of a laundry dryer 1 and includes a front panel 11 defining a front surface of the laundry dryer 1, a rear panel 12 defining a rear surface of the laundry dryer 1, a pair of side panels 14 defining side surfaces of the laundry dryer 1, and a top panel 13 defining a top surface of the laundry dryer 1.

The front panel 11 can include an inlet 111 defined therein to be in communication with a drum 20 to be described later, and a door 112 pivotably coupled to the cabinet 10 to open and close the inlet 111.

In some examples, a control panel 117 can be disposed on the front panel 11.

For example, the control panel 117 can include input device 118 for receiving a control command from a user, output device 119 for outputting information such as the control command or the like selectable by the user, and a main controller that controls a command to perform a cycle of the laundry dryer.

In some examples, the input device 118 can include power supply requesting device for requesting power supply to the laundry dryer, course input device for allowing the user to select a course among multiple courses, execution requesting device for requesting start of the course selected by the user, and the like.

The output device 119 can include at least one of a display panel capable of outputting characters and/or figures, and a speaker capable of outputting audio signals and sounds. The user can easily identify a current situation of the ongoing cycle, a remaining time, and the like via the information output via the output device 119.

Inside the cabinet 10, there are the drum 20 rotatably disposed and providing therein a space in which laundry (an object-to-be-dried) is accommodated, a duct assembly 30 for forming a flow path for re-supplying air discharged from the drum 20 to the drum 20, and a heat exchange assembly 40 for dehumidifying and heating air introduced into the duct assembly 30 and then re-supplying the air to the drum 20.

The drum 20 includes a cylindrical drum body 21 with an open front surface. Inside the cabinet 10, a first support 22 for rotatably supporting the front surface of the drum body 21, and a second support 23 for rotatably supporting a rear surface of the drum body 21 can be disposed.

The first support 22 can include a first fixed body 22a fixed inside the cabinet 10, a drum inlet 22b defined to extend through the first fixed body 22a to allow the inlet 111 and an interior of the drum body 21 to communicate with each other, and a first support body 22c disposed on the first fixed body 22a and inserted into the front surface of the drum body 21.

The first support 22 can further include a connecting body 22d for connecting the inlet 111 and the drum inlet 22b to each other. As shown, the connecting body 22d can be formed in a pipe shape extending from the drum inlet 22b toward the inlet 111. In addition, the connecting body 22d can have an air outlet 22e in communication with the duct assembly 30.

As shown in FIG. 2, the air outlet 22e as a passage that allows internal air of the drum body 21 to flow to the duct assembly 30 can be defined as a through-hole defined to extend through the connecting body 22d.

The second support 23 includes a second fixed body 23a fixed inside the cabinet 10, and a second support body 23b disposed on the second fixed body 23a and inserted into the rear surface of the drum body 21.

The second support 23 has an air inlet 23c defined to extend through the second fixed body 23a so as to allow the interior of the drum body 21 to be in communication with the interior of the cabinet 10.

In some implementations, the duct assembly 30 can connect the air outlet 22e and the air inlet 23c to each other.

The cylindrical drum body 21 can be rotated via a driver 50 of various shapes.

In some implementations, as shown in FIG. 2, the driver 50 can include a drum motor 51 fixed inside the cabinet 10, a pulley 52 rotated by the drum motor 51, and a belt 53 for connecting a circumferential surface of the pulley 52 and a circumferential surface of the drum body 21 to each other.

In some examples, the first support 22 can have a first roller R1 for rotatably supporting the circumferential surface of the drum body 21, and the second support 23 can have a second roller R2 for rotatably supporting the circumferential surface of the drum body 21.

However, the present disclosure is not limited thereto. For instance, a direct drive-type driver that rotates the drum as the drum motor 51 is directly connected to the drum without via the pulley and the belt is also applicable. This naturally falls within the scope of the present disclosure. For convenience, a description will be made based on the illustrated implementation of the driver 50.

In some implementations, the duct assembly 30 includes an exhaust duct 31 connected to the air outlet 22e, a supply duct 32 connected to the air inlet 23c, and a connecting duct 33 that connects the exhaust duct 31 and the supply duct 32 to each other and has the heat exchange assembly 40 installed therein.

The heat exchange assembly 40 can be formed as various apparatuses capable of sequentially dehumidifying and heating air introduced into the duct assembly 30. For example, the heat exchange assembly 40 can be formed as a heat pump system.

As the heat pump system, the heat exchange assembly 40 can include a circulation fan 43 for moving air along the duct assembly 30, a first heat exchanger (a heat absorber 41) that performs a dehumidifying function by lowering humidity of air introduced into the duct assembly 30, and a second heat exchanger (a heater 42) that is disposed inside the duct assembly 30 and heats air that has passed through the first heat exchanger 41.

The circulation fan 43 is constructed to include an impeller 43a disposed in the duct assembly 30, and an impeller motor 43b for rotating the impeller 43a, and provides a flow force to the air moving along the duct assembly 30.

The impeller 43a can be installed at any position among the exhaust duct 31, the connecting duct 33, and the supply duct 32. FIG. 2 shows an implementation in which the impeller 43a is disposed in the connecting duct 33. The present disclosure is not limited thereto, but for convenience, a description will be made below based on the implementation in which the impeller 43a is disposed in the connecting duct 33.

The heat exchange assembly 40 can exchange heat with air circulated along the duct assembly 30.

The heat absorber 41 and the heater 42 are sequentially arranged inside the connecting duct 33 along a direction from the exhaust duct 31 to the supply duct 32, and are connected to each other via a refrigerant pipe 44 for forming a circulation flow path of a refrigerant.

The heat absorber 41 is configured to cool air and evaporate the refrigerant by transferring a heat of air introduced into the exhaust duct 31 to the refrigerant (hereafter, referred to as an evaporator 41).

The heater 42 is configured to heat air and condensing the refrigerant by transferring a heat of the refrigerant that has passed through a compressor 45 to air (hereinafter, referred to as a condenser 42).

The compressor 45 compresses the refrigerant that exchanges the heat with air circulated along the duct assembly 30 by receiving a rotational force by the compressor motor 45a.

In some examples, moisture contained in air moves along a surface of the evaporator 41 when passing through evaporator 41 and is collected on a bottom surface of the connecting duct 33.

In some examples, in order to collect condensate that is condensed from air passing through the evaporator 41 and collected on the bottom surface of the connecting duct 33, the laundry dryer 1 according to the present disclosure has a water collecting portion 60.

The condensate condensed in the evaporator 41 can be primarily collected in the water collecting portion 60, and then can be secondary collected in a water storage 70. The water collecting portion 60 can be located inside the connecting duct 33 as shown, or can be formed separately in a space spaced apart from the connecting duct 33.

The condensate primarily collected via the water collecting portion 60 is supplied to the water storage 70 via a condensate supply pipe 61. In some examples, the condensate supply pipe 61 has a drain pump 62 for smooth discharge of the condensate.

The water storage 70 includes a water storage tank 72 that is constructed to be extended from one side of the front panel 11 to the outside. The water storage tank 72 collects the condensate delivered from the water collecting portion 60 to be described later.

The user can extend the water storage tank 72 from the cabinet 10 to remove the condensate and then re-install the water storage tank 72 in the cabinet 10. Accordingly, the laundry dryer according to the present disclosure can be disposed at any place where a sewer or the like is not installed.

More specifically, the water storage 70 can include the water storage tank 72 that is detachably disposed in the cabinet 10 to provide a space for storing water, and an inlet 72a defined to extend through the water storage tank 72 to introduce water discharged from the condensate supply pipe 61 into the water storage tank 72.

The water storage tank 72 can be formed as a tank in a form of a drawer extendable from the cabinet 10. In some examples, the front panel 11 of the cabinet has a water storage mounting hole defined therein into which the water storage tank 72 is inserted.

A panel 71 is fixed to the front surface of the water storage tank 72. The panel 71 can be detachably coupled to the water storage mounting hole to form a portion of the front panel 11.

The panel 71 can further include a groove 71a into which a user's hand is inserted to grip the panel 71. In some examples, the panel 71 also functions as a handle for extending the water storage tank 72 from the cabinet or retracting the water storage tank 72 into the cabinet.

The inlet 72a is defined to receive the condensate discharged from a condensate nozzle fixed to the cabinet 10. The condensate nozzle can be fixed to the top panel 13 of the cabinet 10 so as to be located above the inlet 72a when the water storage tank 72 is inserted into the cabinet 10.

The user can drain water inside the water storage tank 72 by extending the water storage tank 72 from the cabinet 10 and then turning or tilting the water storage tank 72 in a direction in which the inlet 72a is located. A communication hole 72b defined to extend through a top surface of the water storage tank 72 can be further included such that water inside the water storage tank 72 is easily discharged via the inlet 72a.

In addition, the laundry dryer 1 according to the present disclosure has first filtration device F1 and second filtration device F2 for removing foreign substances such as lint and dust generated in a drying process of an object to be washed such as the laundry.

The first filtration device F1 is disposed in the exhaust duct 31 to primarily filter foreign substances contained in air discharged from the drum 20.

The second filtration device F2 is disposed downstream of the first filtration device F1 in a flow direction of air so as to secondarily filter foreign substances contained in air that has passed through the first filtration device F1. In more detail, as shown, the second filtration device F2 can be disposed upstream of the first heat exchanger 41 inside the connecting duct 33. This is to prevent the foreign substances contained in air from accumulating in the first heat exchanger 41 acting as the heat absorber and contaminating the first heat exchanger 41 or causing performance degradation of the first heat exchanger 41.

As for detailed configurations of the first filtration device F1 and the second filtration device F2, any devices known in the art can be applied, so that a description of the detailed configurations thereof will be omitted.

In some examples, the laundry dryer 1 according to the present disclosure further includes a water supply 80 including an internal water supply 81 and an external water supply 82, and steam supply 90 for receiving water from the water supply 80 and generating steam.

The steam supply 90 can generate steam by receiving fresh water, not the condensate. The steam supply 90 can generate steam by heating water, using an ultrasonic wave, or vaporizing water.

The steam supply 90 can be controlled to supply steam into the drum body 21 by receiving water via the external water supply 82 as well as the internal water supply 81 as needed.

The external water supply 82 can include a direct water valve 82a adjacent to the rear panel 12 or fixed to the rear panel 12, and a direct water pipe 82b for supplying water transferred from the direct water valve 82a to the steam supply 90.

The direct water valve 82a can be coupled to an external water supply source. For example, the direct water valve 82a can be coupled to a water supply pipe extending to the rear surface of the cabinet. Accordingly, the steam supply 90 can receive water directly via the direct water valve 82a.

Therefore, even when the internal water supply 81 is omitted or no water is stored in the internal water supply 81, the steam supply 90 can be configured to receive water for the steam generation via the direct water valve 82a.

The direct water valve 82a can be directly controlled by a controller 100.

The controller 100 can be installed on the control panel 117, but can be formed as a separate control panel as shown in FIG. 1 so as to prevent overload of the control panel 117 and so as not to increase a manufacturing cost.

In some examples, the controller 100 can be disposed adjacent to the steam supply 90. The controller 100 can be disposed on the side panel 14 on which the steam supply 90 is installed so as to reduce a length of a control line or the like connected to the steam supply 90.

In some examples, the steam supply 90 can be installed adjacent to the direct water valve 82a. Accordingly, residual water can be prevented from unnecessarily remaining in the direct water pipe 82b, and water can be supplied immediately.

The controller 100 can be configured to control an operation of the laundry dryer 1 based on an input of the user applied via the input device 118. The controller 100 can be composed of a printed circuit board and elements mounted on the printed circuit board. When the user inputs the control command such as selecting a laundry treatment course, operating the laundry dryer 1, or the like via the input device 118, the controller 100 can control the operation of the laundry dryer 1 based on a preset algorithm.

Specific control content of the controller 100 in the present disclosure will be described later.

Figure 3:
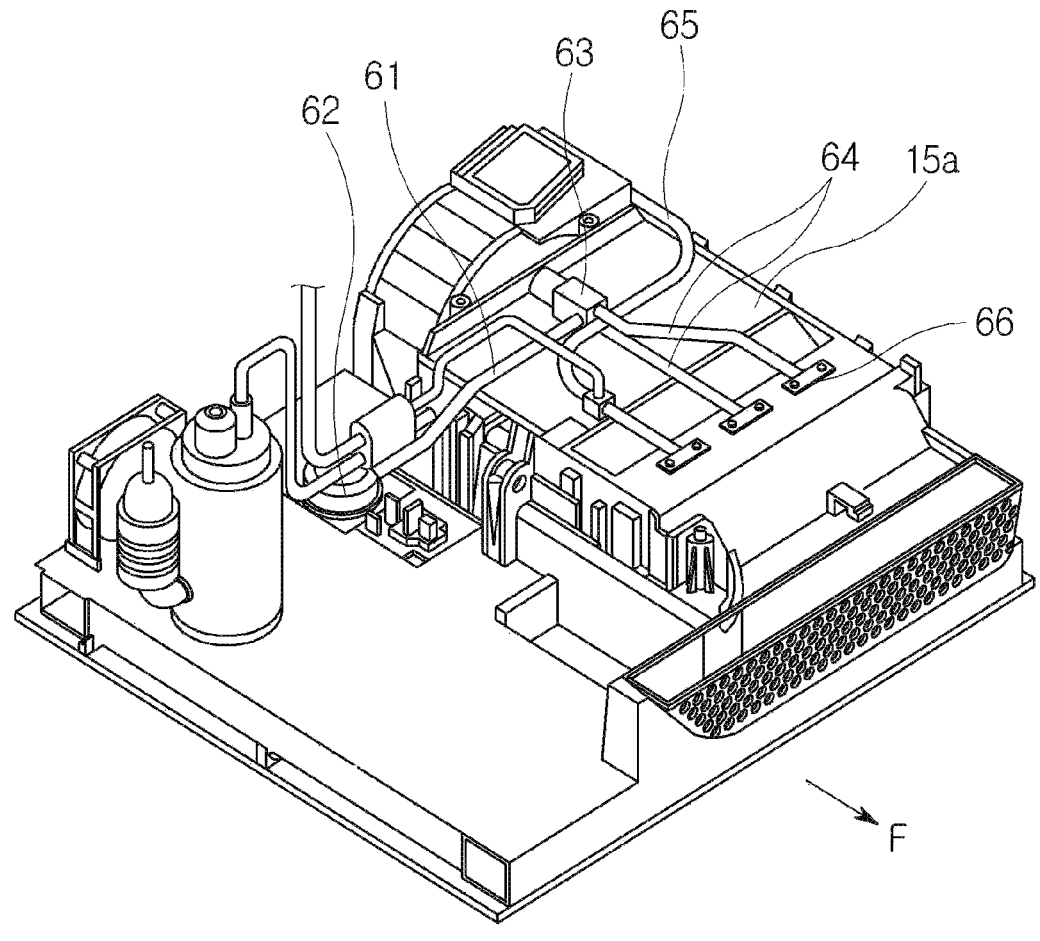
FIG. 3 is a perspective view showing an example of an internal structure of the laundry dryer.

In some examples, FIG. 3 is a perspective view showing an example of an internal structure of the laundry dryer.

A bottom panel 15 is constructed to support mechanical elements of the laundry dryer 1, including the heat exchange assembly 40. For mounting of the machine elements, the bottom panel 15 forms multiple mounting portions. The mounting portion refers to an area defined for the mounting of the machine elements. The mounting portions can be divided from each other by a step of the bottom panel. Hereinafter, components will be described in a counterclockwise direction with respect to the connecting duct 33.

Unlike the drum 20 being disposed at a center in a left and right direction of the laundry dryer 1, an air circulation flow path is eccentrically disposed to a left or right side of the drum 20. The eccentric disposition of the air circulation flow path is for efficient drying of an object-to-be-treated and an efficient arrangement of the parts.

An entrance of the connecting duct 33 is disposed beneath the exhaust duct 31, and is connected to the exhaust duct 31. An entrance 33a of the connecting duct 33 is formed to guide air in an inclined direction together with the exhaust duct 31. For example, the entrance of the connecting duct 33 becomes narrower in a downward direction. In particular, a left side surface of the entrance is inclined in a rightward and downward direction. When the air circulation flow path is disposed on a lower left side of the drum 20, a right side surface of the entrance will be inclined in a leftward and downward direction.

The evaporator 41, the condenser 42, and the circulation fan 43 are sequentially arranged on a downstream side of the entrance based on the flow of air. When the laundry dryer 1 is viewed from the front, the condenser 42 is disposed behind the evaporator 41, and the circulation fan 43 is disposed behind the condenser 42. The evaporator 41, the condenser 42, and the circulation fan 43 are respectively mounted in the mounting portions defined in the bottom panel 15.

A base cover 15a can be installed on the evaporator 41 and the condenser 42. The base cover 15a can be composed of a single member or multiple members.

The heat exchange assembly 40 can include the evaporator 41, the condenser 42, and the compressor 45 to constitute one heat pump system. A brief description of the heat pump system is as follows.

The refrigerant evaporates (a liquid phase—>a gaseous phase) while absorbing heat in the evaporator 41, and becomes a gaseous state of a low-temperature and a low-pressure and is sucked into the compressor 45. In the compressor 45, the refrigerant in the gaseous phase becomes in a high-temperature and high-pressure state while being compressed, and flows to the condenser 42. In the condenser 42, the refrigerant is liquefied while releasing heat. The liquefied high-pressure refrigerant is decompressed in an expander. The low-temperature and low-pressure refrigerant in the liquid state enters the evaporator 41.

Hot dry air is supplied to the drum 20 through the supply duct 32 so as to dry the object-to-be-dried. The hot dry air evaporates moisture of the object-to-be-treated and becomes hot and humid air. The hot and humid air is recovered through the exhaust duct 31, and receives heat of the refrigerant via the evaporator 41 to become low-temperature air. As a temperature of the air decreases, an amount of saturated vapor in the air decreases, and vapor contained in the air is condensed. Then, the low-temperature dry air receives the heat of the refrigerant via the evaporator 41, becomes high-temperature dry air, and is supplied to the drum 20 again.

The base cover 15a is formed to cover the evaporator 41 and the condenser 42. The base cover 15a can be coupled to steps or sidewalls of the bottom panel 15 formed on left and right sides of the evaporator 41 and the condenser 42 to form a portion of the connecting duct 33.

The circulation fan 43 is covered by the bottom panel 15 and a circulation fan cover. An exit of the circulation fan cover is formed above the circulation fan 43. The exit is connected to the supply duct 32. The hot dry air generated by the heat exchange assembly 40 is supplied to the drum 20 through the supply duct 32.

The circulation fan 43 is located at a rearmost portion of the cabinet 10. In the air circulation flow path, the circulation fan 43 is disposed on a downstream side of the condenser 42 based on the flow of air. The circulation fan 43 can be formed as a centrifugal fan. The centrifugal fan is constructed to suck air in an axial direction and blows air in a radial direction. When a rotational axis of the circulation fan 43 is disposed to extend toward the condenser 42, the condenser 42 is disposed on a line in which the rotational axis of the circulation fan 43 extends.

The circulation fan 43 sucks the hot dry air from the condenser 42. In addition, the hot dry air sucked by the circulation fan 43 is ejected to the exit of the circulation fan cover formed above the circulation fan 43. The centrifugal fan generates a great wind volume and a high wind speed based on a strong suction power than an axial fan.

The drain pump 62 is installed on one side of the condenser 42 or one side of the circulation fan 43. The drain pump 62 is constructed to transfer the collected condensate to the mounting portion where the drain pump 62 is installed.

The bottom panel 15 is formed to drain the condensate generated during the operation of the heat exchange assembly 40 to the water collecting portion 60 where the drain pump 62 is installed. For example, a bottom surface of the mounting portion can be inclined to allow the condensate to flow into the mounting portion where the drain pump 62 is installed, or a height of a step of the water collecting portion 60 where the drain pump 62 is installed can be partially small.

When air circulating in the drum 20 exchanges heat in the heat exchange assembly 40, condensation occurs and the condensate falls to a bottom surface of the bottom panel 15. Thus, the condensate is collected in the mounting portion at a bottom of the condenser 42. In some examples, the mounting portion in which the condenser 42 is installed is defined adjacent to the water collecting portion 60 in which the drain pump 62 is installed with a partition wall forming the air circulation flow path therebetween.

The partition wall has a flow path formed to pass through the partition wall such that the condensate collected in the mounting portion where the condenser 42 is installed can flow to the water collecting portion 60. The water collecting portion 60 is formed at a vertical level lower than that of a bottom surface of the mounting portion of the heat exchange assembly 40. Accordingly, the flow path is inclined downward from the water collecting portion 60 toward the mounting portion of the heat exchange assembly 40.

The condensate collected in the water collecting portion 60 where the drain pump 62 is installed can be transferred to the water storage 70 by the drain pump 62 by such structure of the bottom panel 15. In addition, the condensate can be transferred by the drain pump 62 and used for washing the evaporator 41 or the condenser 42.

The drain pump 62 is connected to a control valve 63 by a condensate supply pipe 61. When the drain pump 62 operates, the condensate collected in the water collecting portion 60 is transferred to the control valve 63. The control valve 63 is formed to distribute the condensate transferred by the drain pump 62 to a washing water supply pipe 64 and a drain pipe 65.

The washing water supply pipe 64 and the drain pipe 65 connected to the control valve 63 can be made of a flexible material.

The drain pipe 65 is connected to the control valve 63 and the water storage tank 72. The drain pipe 65 is not directly connected to the water storage tank 72, but is connected to the water storage tank 72 via an upper portion of a water container support frame.

When the condensate transferred by the drain pump 62 flows into the drain pipe 65 by the operation of the control valve 63, the condensate flows into the water storage tank 72 along the drain pipe 65. The condensate is temporarily stored in the water storage tank 72 until the user empties the water storage tank 72.

The washing water supply pipe 64 is connected to the control valve 63 and a washing water sprayer 66. The washing water sprayer 66 is constructed to spray the condensate onto a surface of the evaporator 41 or the condenser 42. As an operating time of the laundry dryer 1 is accumulated, dust or foreign substances can adhere to the surfaces of the evaporator 41 and the condenser 42. Because the dust or the foreign substances cause deterioration of heat exchange efficiencies of the evaporator 41 and the condenser 42, the dust or the foreign substances need to be removed promptly.

When the condensate is supplied to the washing water sprayer 66 through the washing water supply pipe 64, the washing water sprayer 66 sprays the received condensate to the evaporator 41 or the condenser 42.

For this purpose, a nozzle of the washing water sprayer 66 is disposed to face toward the evaporator 41 or the condenser 42. When the condensate is sprayed into the evaporator 41 or the condenser 42 through the nozzle, the dust or the foreign substances can be removed from the evaporator 41 or the condenser 42.

The washing water supply pipe 64 and the washing water sprayer 66 can respectively include a plurality of washing water supply pipes and a plurality of washing water sprayers so as to spray the condensate over a large area.

As described above, in the present disclosure, the water collecting portion 60, the condensate supply pipe 61, the drain pump 62, the control valve 63, the washing water supply pipe 64, the drain pipe 65, and the washing water sprayer 66 can be connected to each other so as to constitute washing device 200 that can use the condensate stored in the cabinet 10 as washing water, and can spray the washing water toward the surface of the heat exchange assembly 40 to remove the foreign substances, the bacteria, and the like.

Figure 4:
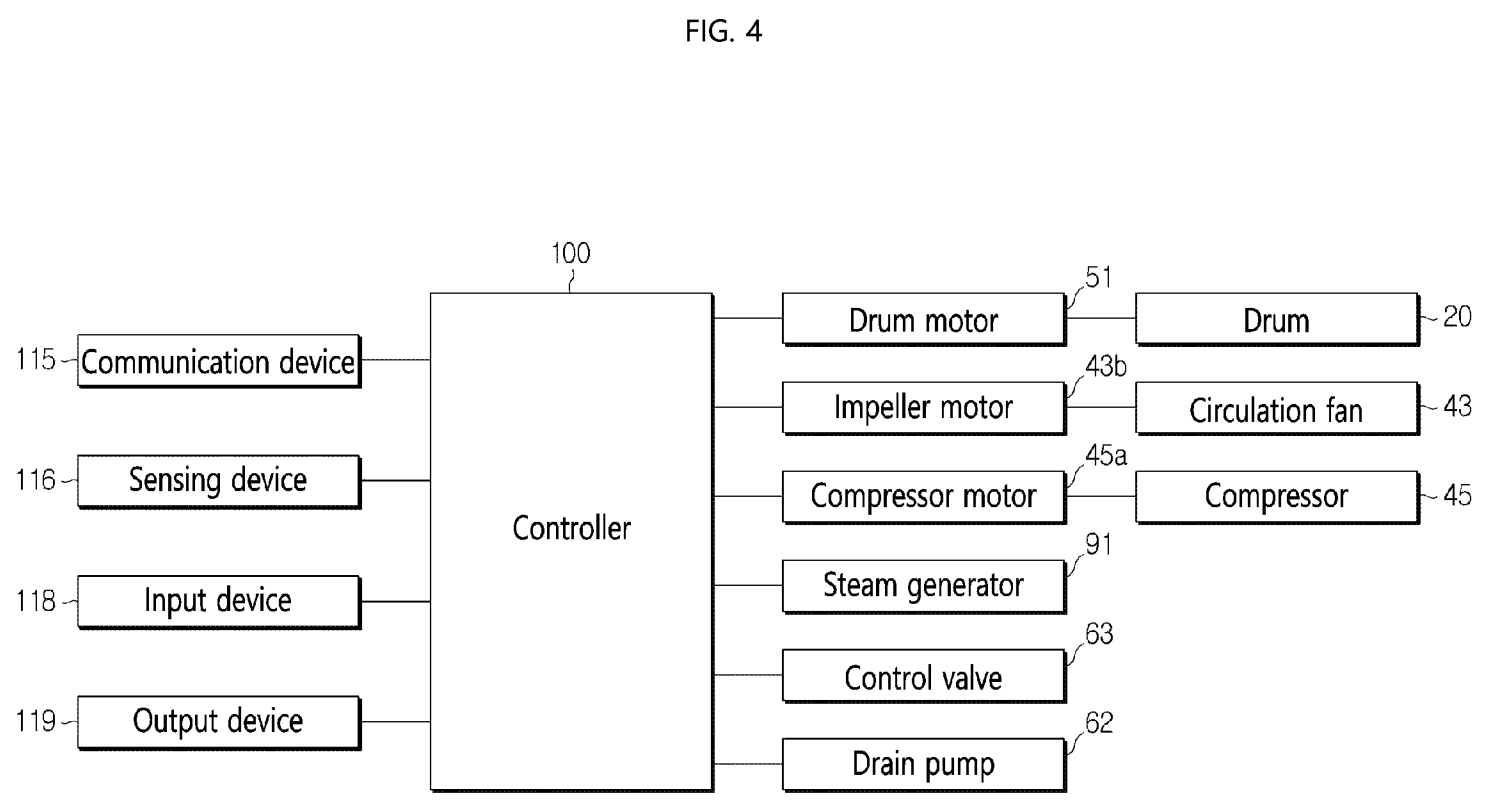

In some examples, FIG. 4 is a block diagram for illustrating a control configuration in a laundry dryer.

Referring to FIG. 4, the laundry dryer 1 can include at least one of the input device 118, the output device 119, communication device 115, sensor 116, motors 51, 43_b_, and 45_a_, a drain pump 62, the steam supply 90, and the controller 100.

The input device 118 can receive a control command related to the operation of the laundry dryer 1 from the user. The input device 118 can be composed of a plurality of buttons or can be composed of a touch screen.

Specifically, the input device 118 can be formed in a shape to receive selection of a driving course of the laundry treating apparatus or receive a control input related to execution of the selected driving course.

The output device 119 can output information related to the operation of the laundry dryer 1. The output device 119 can include at least one display.

The information output by the output device 119 can include information related to an operating state of the laundry dryer 1. That is, the output device 119 can output information related to at least one of the selected driving course, whether a failure has occurred, a driving completion time, and an amount of laundry accommodated in the drum 20.

As an example, the output device 119 can be a touch screen integrally formed with the input device 118.

The communication device 115 can be in communication with an external network. The communication device 115 can receive the control command related to the operation of the laundry treating apparatus from the external network. For example, the communication device 115 can receive an operation control command of the laundry dryer transmitted from an external terminal via the external network. This allows the user to remotely control the laundry dryer.

In addition, the communication device 115 can transmit information related to an operation result of the laundry treating apparatus to a predetermined server via the external network.

In addition, the communication device 115 can be in communication with another electronic device in order to establish an Internet of Things (JOT) environment.

The sensor 116 can sense the information related to the operation of the laundry dryer.

Specifically, the sensor 116 can include at least one of a current sensor, a voltage sensor, a vibration sensor, a noise sensor, an ultrasonic sensor, a pressure sensor, an infrared sensor, a visual sensor (a camera sensor), an electrode sensor, and a temperature sensor.

For example, the current sensor of the sensor 116 can sense a current flowing at a point of a control circuit of the laundry dryer 1.

As another example, the temperature sensor of the sensor 116 can sense a temperature in the duct assembly 30 and can sense a temperature in the drum 20.

The sensor 116 can include one or more temperature sensors that sense a temperature of the heat exchange assembly 40 and transmit the sensed result to the controller 100.

As an example, the sensor 116 can include the one or more temperature sensors to sense one or more of temperatures of air and the refrigerant respectively circulating in the first heat exchanger 41 and the second heat exchanger 42.

As another example, the sensor 116 can include the one or more temperature sensors to sense a temperature of the refrigerant circulating in the compressor 45.

The sensor 116 can further include a plurality of temperature sensors for sensing a temperature of air flowing into or out of the drum 20.

As such, the sensor 116 including the plurality of temperature sensors can be formed in a shape in which a sensing module for sensing the temperature is disposed in the heat exchange assembly 40 and a sensing module for receiving the sensed result of the plurality of temperature sensors and sensing the temperature is disposed in the controller 100.

As described above, the sensor 116 can include at least one of the various types of sensors, and the types of sensors equipped in the laundry dryer 1 are not limited. In addition, the number or installation locations of respective sensors can be designed in various ways depending on a purpose.

The motors 51, 43_b_, and 45_a_ can include a drum motor 51, an impeller motor 43_b_, and a compressor motor 45_a_, and can vary at least one of power, current, voltage, and speed in response to a control command (a command) of the controller 100.

In some examples, the drum motor 51 can vary a rotation speed (e.g., revolutions per minute (rpm)) of the drum motor 51 in response to the control command of the controller 100, and vary a rotation speed (rpm) of the drum 20 connected to an output shaft of the drum motor 51.

As another example, the impeller motor 43_b_ can vary a rotation speed (rpm) of the circulation fan 43 in response to the control command of the controller 100.

As another example, the compressor motor 45_a_ can vary a frequency (Hz) of the compressor 45 in response to the control command of the controller 100.

The steam supply 90 can be controlled to supply steam into the drum body 21 by receiving water via the external water supply 82 as well as the internal water supply 81 as needed.

The steam supply 90 can include a steam generator 91 for generating steam by heating received water, a steam pipe 92 through which the generated steam flows, and a steam nozzle 93 for spraying steam into the drum body 21.

As an example, the steam generator 91 is expressed to use a scheme (hereinafter, referred to as a 'whole heating scheme' for convenience) of generating steam by heating a certain amount of water contained therein with a heater, but is not limited thereto.

The controller 100 can control the component included in the laundry dryer 1.

In some implementations, the controller 100 can generate at least one of a power command value, a current command value, a voltage command value, and a speed command value in order to control rotation of the drum motor 51, the impeller motor 43b, and the compressor motor 45a.

In some examples, in the present disclosure, the controller 100 can control the drum motor 51, the impeller motor 43b, and the compressor motor 45a, independently.

Accordingly, the controller 100 can control an operation of at least one of the drum 20, the circulation fan 43, and the heat exchange assembly 40 based on the control input that is input to the input device 118.

That is, the controller 100 can control the rotation speed and a rotation pattern of the drum 20 based on the control input of the user input to the input device 118. In addition, the controller 100 can control the rotation speed or an operation time point of the circulation fan 43 based on the control input of the user input to the input device 118.

In some examples, the drum and the circulation fan are connected to one motor. Therefore, the drum and the circulation fan can rotate at the same time and stop rotating at the same time.

In some examples, when spraying steam to the laundry dryer, the rotation of the circulation fan can be stopped in order to sufficiently supply the sprayed steam to the object-to-be-dried, and the drum was also stopped to stop the circulation fan.

However, when the drum stops rotating, the object-to-be-dried is not able to be inverted. In addition, even when steam is supplied to the object-to-be-dried, steam is supplied only to objects-to-be-dried located in a direction in which steam is sprayed. Therefore, there was a limit in supplying steam evenly to entire objects-to-be-dried.

In order to solve such problem, in the laundry dryer 1, the drum motor 51 and the impeller motor 43b are formed separately from each other. In addition, the controller 100 can control the drum motor 51, the impeller motor 43b, and the compressor motor 45a, independently.

In addition, the controller 100 can control the heat exchange assembly 40 so as to adjust a temperature inside the drum 20 based on a control input of the user input to the input device 118.

As an example, the controller 100 can control a driving frequency (Hz) of the compressor 45 based on the control input of the user input to the input device 118.

In addition, the controller 100 can generate at least one of a power command value, a current command value, and a voltage command value so as to control the operation of the steam generator 91.

In some examples, in the present disclosure, when at least one of a temperature change and an operating state corresponds to a reference condition after driving the compressor 45, the controller 100 can stop the driving of the compressor 45, so that a surface temperature of the heat exchange assembly 40 becomes equal to or higher than a reference temperature, thereby controlling a sterilization operation to be performed.

Figure 7:
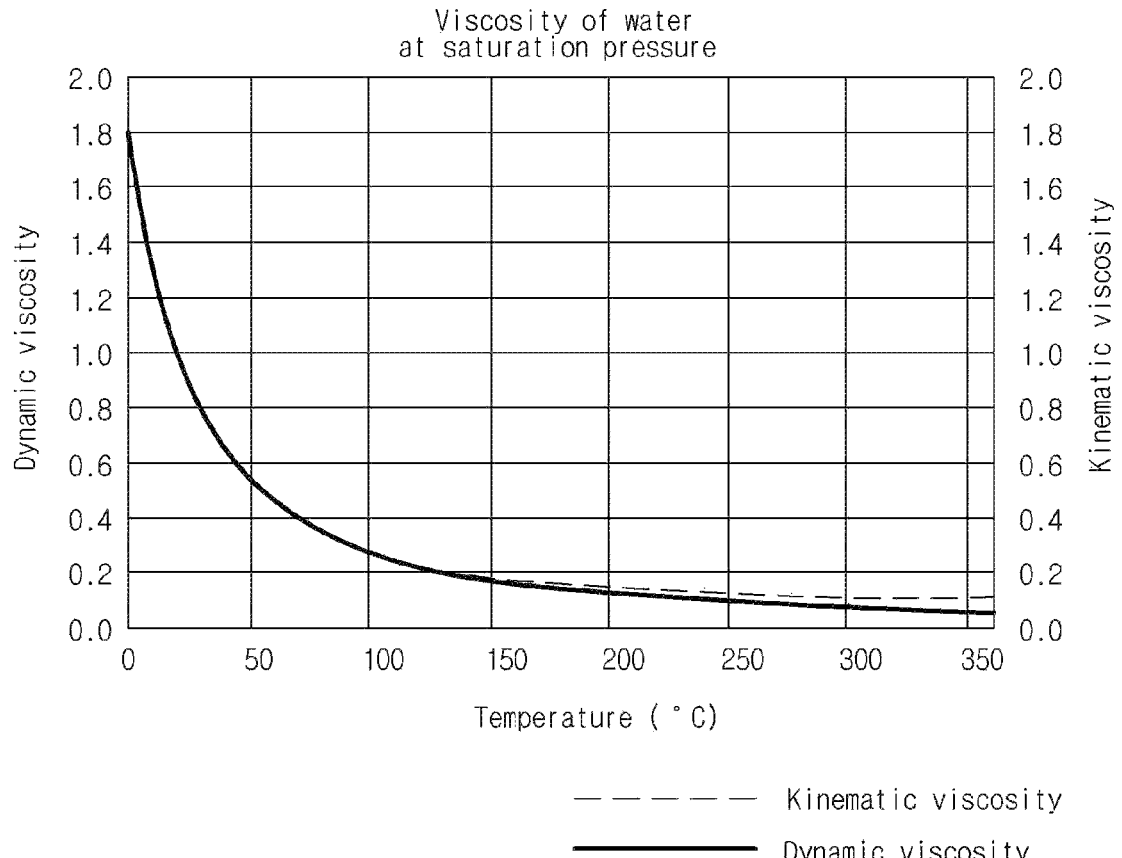
FIG. 7 is a graph showing an example of changes in viscosity of foreign substances and microorganisms based on a temperature in a method for controlling a laundry dryer.

For example, as shown in FIG. 7, after driving the compressor 45, in a cycle stable section in which an operating frequency F of the compressor 45 is a certain frequency for a certain time period, the controller 100 can stop the driving of the compressor 45, so that a surface temperature of the heat exchange assembly 40 becomes a temperature equal to or higher than 60° C., which is the reference temperature.

In some examples, in the present disclosure, the controller 100 can control the drain pump 62 and the control valve 63 to spray washing water into the heat exchange assembly 40.

That is, the controller 100 can control a driving speed (rpm) of the drain pump 62 to move the stored condensate so as to be used as washing water.

In addition, the controller 100 can open and close the control valve 63 to allow washing water moved from the drain pump 62 to flow to the washing water supply pipe 64. That is, the controller 100 can control the control valve 63 to allow the condensate supply pipe 61 and the washing water supply pipe 64 to communicate with each other, or allow the condensate supply pipe 61 and the drain pipe 65 to communicate with each other.

For convenience, in the present disclosure, it is described that the controller 100 allowing the condensate supply pipe 61 and the drain pipe 65 to communicate with each other is set as a default value, and the condensate supply pipe 61 and the washing water supply pipe 64 communicate with each other when the control valve 63 is operated, but the present disclosure is not limited thereto. The condensate supply pipe 61 and the washing water supply pipe 64 being in communication with each other can be set as the default value, and the condensate supply pipe 61 and the drain pipe 65 can communicate with each other by operating the control valve 63.

In the present disclosure, when the washing and sterilization operations for the heat exchange assembly 40 are performed, the controller 100 can operate the steam supply 90 to supply steam, and then drive the compressor 45 to wash and sterilize the heat exchange assembly 40. In some examples, the controller 100 can allow the washing and sterilization operations for the heat exchange assembly 40 to be performed in a state in which the object-to-be-dried is not accommodated in the drum 20.

That is, when the applying power to the steam generator 91 to operate the steam supply 90, the controller 100 can drive the circulation fan 43 to allow steam to flow to the heat exchange assembly 40, and can rotate the drum 20. In some examples, the controller 100 can rotate the circulation fan 43 at a preset first circulation speed V1.

In addition, when operating the steam supply 90, the controller 100 can control the steam generator 91 to spray steam for a preset spray time ts, then stop the steam spraying for a preset pause time tp, and then respray steam for the spray time ts.

In addition, the controller 100 can stop the driving of the compressor 45 when operating the steam supply 90 in order to prevent the power supply from being cut off due to an instantaneous and sudden increase in the power consumption of the entire laundry dryer 1. Specifically, when driving the steam generator 91 to preheat water or generate steam, the controller 100 can stop the rotation of the compressor motor 45a.

In some examples, the controller 100 can control the operation of the washing device 200, so that the washing water is sprayed to the heat exchange assembly 40 based on a preset spray standard after the supply of steam is terminated. In addition, when the operation of the washing device 200 is started, the controller 100 can drive the compressor 45 at a preset first compression frequency f1.

In some examples, after the operation of the washing device 200 is terminated, the controller 100 can accelerate the compressor 45 and drive the compressor 45 at a preset second compression frequency f2. In some examples, the controller 100 can rotate the circulation fan 43 at a preset second circulation speed V2.

The controller 100 can operate the drain pump 62 for a washing time tw input in advance after the supply of steam is terminated.

In some examples, the control of the controller 100 over time will be described later with reference to FIGS. 5 to 6B.

Figure 5:
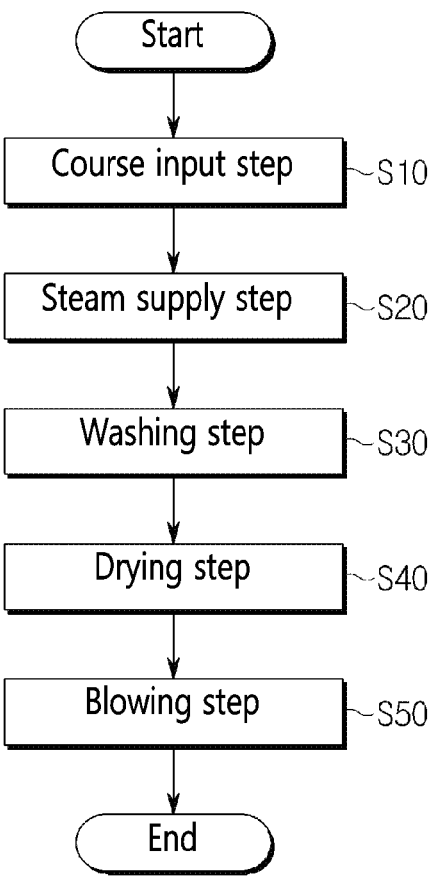
FIG. 5 is a flowchart illustrating an example of a method for controlling the laundry dryer.
Figure 6A:
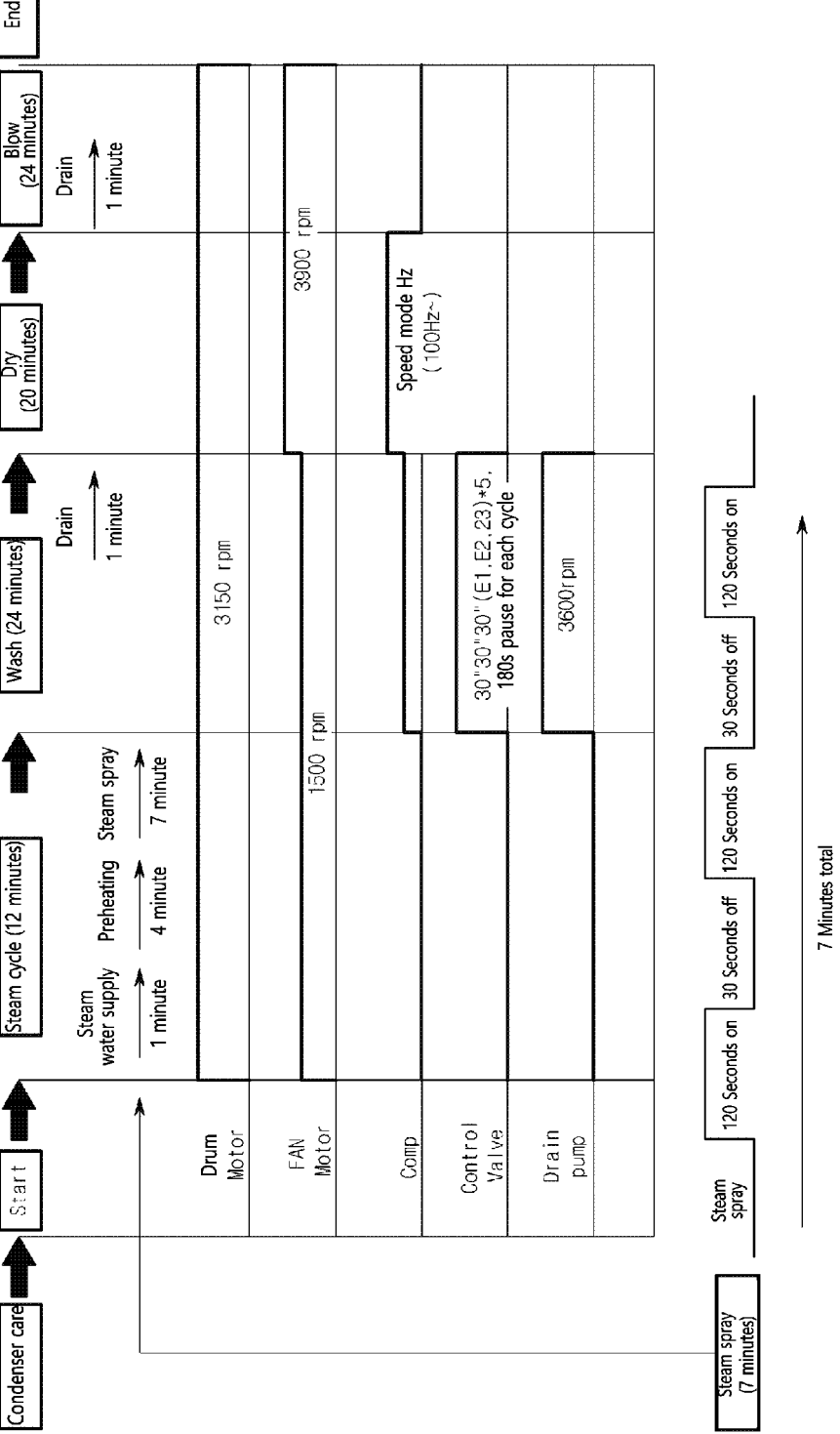
FIGS. 6A and 6B are illustrative views showing examples of a steam drying method.
Figure 6B:
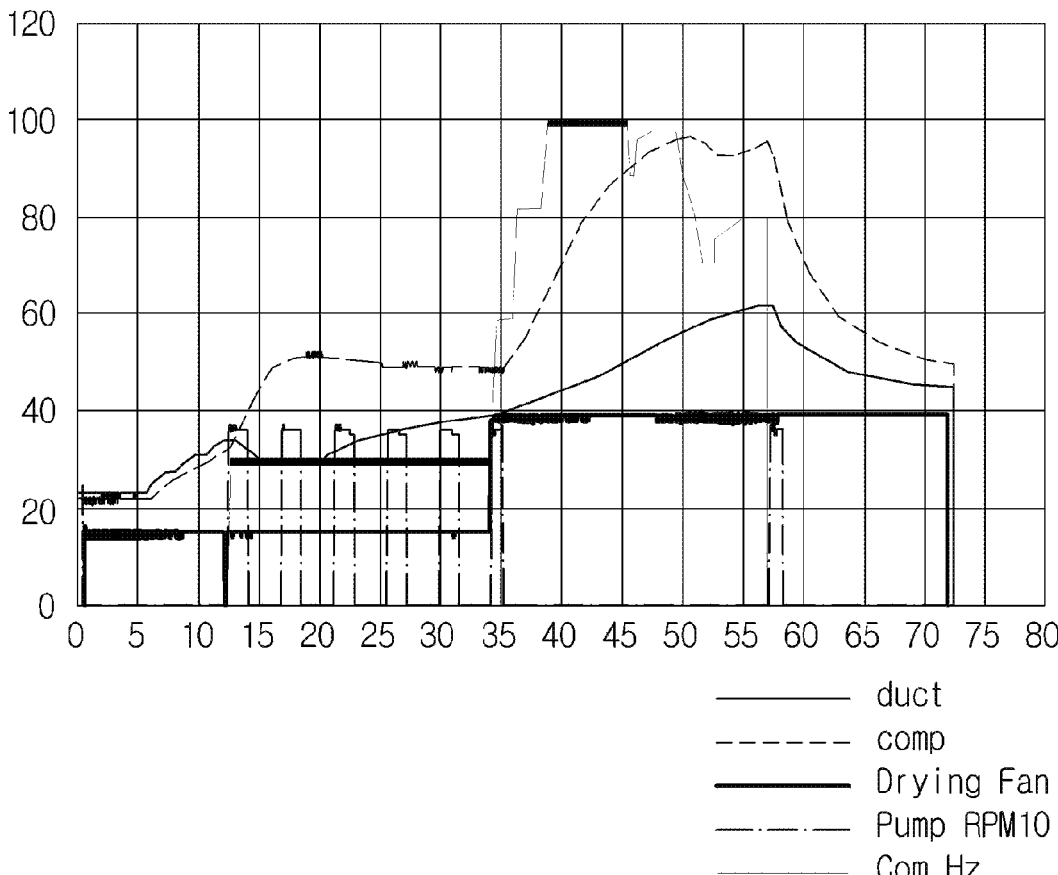

FIG. 5 is a flowchart illustrating an example of of a method for controlling a laundry dryer, and FIGS. 6A and 6B are illustrative views showing examples of a steam drying method.

Referring to FIGS. 1 to 6B, a method controls the laundry dryer 1 as follows.

In some implementations, the method for controlling the laundry dryer 1 can include a course input step (S10), a steam supply step (S20), a washing step (S30), a drying step (S40), and a blowing step (S50).

In the course input step (S10), a control input for performing a condenser care course for washing and sterilizing the heat exchange assembly is input.

That is, when the laundry dryer 1 of the present disclosure is turned on, the user can input the control input to the input device 118. In some examples, the user can input the condenser care course to perform the wash and the sterilization on the foreign substances, the microorganisms, and the like that can exist in the heat exchange assembly 40 using the laundry dryer 1.

In some examples, in the condenser care course, the washing and sterilization operations of the heat exchange assembly 40 can be performed in the state in which the object-to-be-dried is not accommodated in the drum 20.

In the steam supply step (S20), the controller 100 can control the steam supply 90 to supply steam to the heat exchange assembly 40.

In the steam supply step (S20), the controller 100 can rotate the drum motor 51 at a reference speed Wr input in advance (S21). For example, the controller 100 can continuously rotate the drum motor 51 while maintaining the rotation speed of the drum motor 51 at a speed equal to or higher than 3000 rpm and equal to or lower than 3300 rpm, thereby continuously rotating the drum 20 at a constant speed.

In the present disclosure, the drum 20 rotates in the state in which the object-to-be-dried is not accommodated in the drum 20. This is to prevent steam from condensing on the surface of the drum 20 when steam is sprayed while the drum 20 is not rotating and is still.

In the steam supply step (S20), the controller 100 does not drive the compressor 45 in order to prevent the instantaneous increase in the power consumption of the laundry dryer 1 (S22).

In the steam supply step (S20), the controller 100 can rotate the circulation fan 43 at the preset first circulation speed V1 (S23).

As an example, in the steam supply step (S20), the controller 100 can drive (rotate) the circulation fan 43 at a speed equal to or higher than 1000 rpm and equal to or lower than 2000 rpm.

In some examples, in the steam supply step (S20) of the present disclosure, the controller 100 can supply steam into the drum 20 in order to supply steam to the heat exchange assembly 40 (S24).

The steam supply step (S20) can include a steam water supply step (S24a), a steam preheating step (S24b), and a steam spraying step (S24c).

In the steam water supply step (S24a), the controller 100 can supply water from the water supply 80 to the steam supply 90. In some examples, the controller 100 can supply water into the steam generator 91 by operating a water supply pump disposed in the internal water supply 81, or can supply water into the steam generator 91 by opening the direct water valve 82a disposed in the external water supply 82.

For example, in the steam water supply step (S24a), an amount of water equal to or greater than 150 cc and equal to or smaller than 250 cc can be supplied from the water supply 80 to the steam generator 91, and a time for supplying water of the water supply 80 to the steam generator 91 can be 30 seconds or longer and 1 minute and 30 seconds or shorter.

In the steam preheating step (S24b), the controller 100 can heat water supplied for the steam generation for a preset preheating time th by applying power to the steam supply 90.

Specifically, in the steam preheating step (S24b), the controller 100 can heat water supplied to the steam generator 91 by applying power to a heater disposed in the steam generator 91. In some examples, the controller 100 can apply power to the heater for the preheating time th, and the preheating time th can be set to be longer than a time for water to reach a boiling point.

For example, in the steam preheating step (S24b), the controller 100 can generate a control command to apply power to the steam supply 90 for 3 minutes and 30 seconds or longer and 4 minutes and 30 seconds or shorter.

In the steam spraying step (S24c), the controller 100 can spray steam generated from the steam supply 90 into the drum 20 by a preset spray amount after the steam preheating step (S24b).

Specifically, in the steam spraying step (S24c), the controller 100 can generate a control command to the steam generator 91 such that water heated in the steam generator 91 and started to boil flows through the steam pipe 92 and is sprayed into the drum body 21 via the steam nozzle 93.

In the steam spraying step (S24c), the controller 100 can spray steam for the preset spray time ts, then stop the spray of steam for the preset pause time tp, and then respray steam for the spray time ts again.

For example, in the steam spraying step (S24c), the controller 100 can spray steam three times, each of which has a duration of the spray time ts. The pause time tp can exist between two spray times ts to stop the spray of steam.

That is, in the steam spraying step (S24c), the controller 100 can spray an amount of water equal to or greater than 150 cc and equal to or smaller than 200 cc from the steam generator 91 into the drum 20 in three times. In some examples, the controller 100 sprays steam into the drum 20 for the time ts of 110 seconds or longer and 130 seconds or shorter (first spray), then stops the spray of steam for the time tp of 20 seconds or longer and 40 seconds or shorter (first pause), then sprays steam into the drum 20 for the time ts of 110 seconds or longer and 130 seconds or shorter again (second spray), and then stops the spray of steam for the time tp of 20 seconds or longer and 40 seconds or shorter (second pause). Finally, the controller 100 sprays steam into the drum 20 for the time is of 110 seconds or longer and 130 seconds or shorter (third spray). As a result, the steam spraying step (S24c) can be composed of the 3 steam spraying steps and the 2 pause steps performed by the controller 100.

In other words, in the steam spraying step (S24c), the controller 100 can heat an amount of water equal to or greater than 50 cc and equal to or smaller than 70 cc in the steam generator 91, vaporize the water to steam, and spray the steam into the drum 20 for each time, and repeat this three times. In addition, there are the first pause time of 20 seconds or longer and 40 seconds or shorter between the first spray and the second spray, and a second pause time of 20 seconds or longer and 40 seconds or shorter between the second spray and the third spray.

Therefore, in the steam supply step (S20), the controller 100 can supply high-temperature steam to the heat exchange assembly 40 by operating the drum 20, the circulation fan 43, and the steam supply 90.

As described above, according to the steam supply step (S20), the high-temperature steam is sprayed into the drum 20, and flows to the heat exchange assembly 40 along the duct assembly 30 by the operation of the circulation fan 43. Accordingly, the high-temperature steam is supplied to foreign substances, the microorganisms, and the like present on the surface of the heat exchange assembly 40, and viscosity and surface tension of the foreign substances and the microorganisms are reduced as shown in FIG. 7. Therefore, according to the steam supply step (S20) of the present disclosure, there is the effect of reducing the viscosity and the surface tension such that the foreign substances and the microorganisms easily fall from the heat exchange assembly 40 as the high-temperature steam is supplied to the heat exchange assembly 40.

In the washing step (S30), the controller 100 can control the washing device 200 to spray washing water onto the heat exchange assembly 40 based on the preset spray standard after the steam supply step (S20).

In the washing step (S30), the controller 100 can rotate the drum motor 51 at the reference speed Wr input in advance (S31). For example, the controller 100 can continuously rotate the drum motor 51 while maintaining the rotation speed of the drum motor 51 at a speed equal to or higher than 3000 rpm and equal to or lower than 3300 rpm, thereby continuously rotating the drum 20 at the constant speed.

In the washing step (S30), the controller 100 can further include a first heating step (S32) for driving the compressor 45 at the preset first compression frequency f1.

For example, in the first heating step (S32), the controller 100 can drive the compressor 45 by maintaining the operating frequency F of the compressor 45 at a frequency equal to or higher than 25 Hz and equal to or lower than 35 Hz.

When the compressor 45 is driven at the first compression frequency f1 in the first heating step (S32), a refrigerant discharge temperature of the compressor 45 can be increased, and the temperatures inside the drum 20 and the duct assembly 30 can be increased as the air and the refrigerant passing through the heat exchange assembly 40 exchange the heat with each other.

In some examples, when the compressor 45 is driven at the first compression frequency f1 in the first heating step (S32), unlike the second compression frequency f2, which will be described later, the power consumption of the compressor 45 is low, so that, even when the drain pump 62 and the control valve 63 are operated, there is no risk of failure or power supply cut off due to the sudden increase in the power consumption.

In the washing step (S30), the controller 100 can rotate the circulation fan 43 at the preset first circulation speed V1 following the steam supply step (S20) (S33).

For example, in the washing step (S30), the controller 100 can drive (rotate) the circulation fan 43 at a speed equal to or higher than 1000 rpm and equal to or lower than 2000 rpm.

Therefore, as the circulation fan 43 rotates along with the driving of the compressor 45, the temperatures inside the drum 20 and the duct assembly 30 can increase while heat-exchanged air circulates. In addition, the circulation fan 43 also rotates at a relatively low speed compared to the second circulation speed V2, which will be described later, so that, even when the drain pump 62 and the control valve 63 are operated, there is no fear of malfunction or power supply cut off due to the sudden increase in the power consumption.

In some examples, in the washing step (S30), the controller 100 can be configured not to operate the steam supply 90 (S34).

In some examples, the washing step (S30) of the present disclosure can further include a pump driving step (S35) of driving the drain pump 62 for a preset washing time tc.

In the pump driving step (S35), the controller 100 rotates the drain pump 62 at a preset driving speed (rpm) for the preset washing time tc to move the stored condensate to the control valve 63 and use the condensate as washing water.

As an example, the controller 100 can rotate the drain pump 62 at a speed equal to or higher than 3000 rpm and equal to or lower than 4000 rpm for 20 minutes or longer and 30 minutes or shorter.

The washing step (S30) of the present disclosure can include a washing water spraying step (S36) of spraying washing water to the heat exchange assembly 40.

In the washing water spraying step (S36), the controller 100 controls the control valve 63 to allow the condensate introduced from the drain pump 62 to flow toward the washing water supply pipe 64.

Specifically, the control valve 63 of the present disclosure can be connected to the condensate supply pipe 61, the washing water supply pipe 64, and the drain pipe 65 to adjust a flow direction of the condensate.

When activating the washing water spraying step (S36), the controller 100 can control the control valve 63 to communicate the condensate supply pipe 61 and the washing water supply pipe 64 to each other. As a result, the condensate to which the flow force has been applied by the drain pump 62 can flow into the washing water supply pipe 64 as the washing water, and can be sprayed onto the heat exchange assembly 40 via the washing water sprayer 66.

In some examples, in the washing water spraying step (S36), the controller 100 can control the control valve 63 based on a preset washing pattern Pc.

For example, the washing pattern Pc can include operating the control valve 63 for a time of 85 seconds or longer and 95 seconds or shorter and stopping the operation of the control valve 63 for a time of 170 seconds or longer and 190 seconds or shorter.

In some examples, the washing pattern Pc can be repeated 5 times in order to increase an amount of washing.

Therefore, according to the present disclosure, the collected condensate can flow to the control valve 63 using the drain pump 62, and the washing water can be sprayed to the heat exchange assembly 40 in response to the operation of the control valve 63.

Therefore, according to the washing water spraying step (S36), washing water with a water pressure equal to or higher than a predetermined water pressure is sprayed to the heat exchange assembly 40, so that the foreign substances including lint and the microorganisms including the bacteria whose viscosity and surface tension are reduced through the steam supply step (S20) are removed from the heat exchange assembly 40.

Therefore, according to the washing step (S30), the foreign substances, the microorganisms, and the like present in the heat exchange assembly 40 are washed and removed.

In some examples, the washing step (S30) can further include a first drainage step (S39) of discharging the washing water (the condensate) collected after the washing for a preset drainage time td.

In the first drain step (S39), the controller 100 can operate the drain pump 62 to move the condensate collected in the water collecting portion 60, and operate the control valve 63 to allow the condensate to flow to the drain pipe 65. Consequently, the condensate can be transferred to the water storage tank 72.

In some examples, the drainage time td can be 50 seconds or longer and 70 seconds or shorter.

In the drying step (S40), in order to dry the heat exchange assembly 40 to which washing water is sprayed in the washing step (S30), the controller 100 can supply hot air into the drum 20 to dry the drum 20 and the duct assembly 30.

In the drying step (S40), the controller 100 can rotate the drum motor 51 at the reference speed Wr input in advance. For example, the controller 100 can continuously rotate the drum motor 51 while maintaining the rotation speed of the drum motor 51 at a speed equal to or higher than 3000 rpm and equal to or lower than 3300 rpm, thereby continuously rotating the drum 20 at the constant speed.

In addition, the drying step (S40) can include a second heating step (S42) in which the controller 100 drives the compressor at a preset second compression frequency f2.

That is, in the second heating step (S42), the controller 100 can drive the compressor 45 by adjusting the operating frequency F of the compressor 45 to the second compression frequency f2 (S42a).

As an example, the controller 100 can drive the compressor 45 by setting a frequency equal to or higher than 85 Hz and equal to or lower than 105 Hz as the operating frequency F.

In some examples, the controller 100 can give a control command to increase an output for driving compressor 45 to the second compression frequency f2 at once. In some examples, the controller 100 can give a control command to increase the rotation speed of the compressor motor 45a over several steps in order to prevent malfunction due to overload of the compressor motor 45a.

As an example, the controller 100 can primarily generate a control command to drive the compressor 45 at a frequency equal to or higher than 55 Hz and equal to or lower than 65 Hz, then secondarily generate a control command to drive the compressor 45 at a frequency equal to or higher than 75 Hz and equal to or lower than 85 Hz, and finally generate a control command to drive the compressor 45 at the second compression frequency f2.

After adjusting the operating frequency F of the compressor 45 to the second compression frequency f2, the controller 100 can sense the temperature inside the drum 20 for energy efficiency and failure prevention, and can drive the compressor 45 while maintaining the operating frequency F of the compressor 45 at a frequency lower than the second compression frequency f2 based on the sensed temperature (S42b).

In some examples, the controller 100 can sense (measure) a temperature of the duct assembly 30 via the sensor 116 installed in the duct assembly 30. In some examples, the sensor 116 installed in the duct assembly 30 can be a temperature sensor.

In some examples, the controller 100 of the present disclosure can terminate the drying step (S40) by stopping the driving of the compressor 45 based on the reference conditions.

The reference conditions can include a condition for each of a change in a temperature of air flowing into the evaporator 41, a change in a temperature of air flowing out of the evaporator 41, a change in a temperature of the refrigerant flowing into the evaporator 41, a change in a temperature of the refrigerant flowing out of the evaporator 41, a change in a temperature of air flowing into the condenser 42, a change in a temperature of air flowing out of the condenser 42, a change in a temperature of the refrigerant flowing into the condenser 42, and a change in a temperature of the refrigerant flowing out of the condenser 42, and a condition for each of an operating time of the compressor 45, an operating section of the compressor 45, and the operating frequency of the compressor 45.

Accordingly, the controller 100 can stop the driving of the compressor 45 when at least one of the conditions for the change in the temperature of air flowing into the evaporator 41, the change in the temperature of air flowing out of the evaporator 41, the change in the temperature of the refrigerant flowing into the evaporator 41, the change in the temperature of the refrigerant flowing out of the evaporator 41, the change in the temperature of air flowing into the condenser 42, the change in the temperature of air flowing out of the condenser 42, the change in the temperature of the refrigerant flowing into the condenser 42, and the change in the temperature of the refrigerant flowing out of the condenser 42, and the operating states including at least one of the operating time of the compressor 45, the operating section of the compressor 45, and the operating frequency of the compressor 45 corresponds to the reference condition.

For example, in a state where a condition in which the change in the temperature of the air flowing into the evaporator 41 is maintained at a temperature equal to or higher than 70 degrees Celsius for 20 minutes or longer is set as the reference condition, when the change in the temperature of the air flowing into the evaporator 41 is maintained at the temperature equal to or higher than 70 degrees Celsius for 20 minutes or longer as a result of determination on the temperature change, because such case corresponds to the reference condition, the controller 100 can stop the driving of the compressor 45.

Alternatively, in a state where a condition in which a change in the operating frequency of the compressor 45 is within a certain range for a certain time is set as the reference condition, when the operating frequency of the compressor 45 changes within the certain range for the certain time as a result of determination on the operating state, because such case corresponds to the condition for the operating frequency among the reference conditions, the controller 100 can stop the driving of the compressor 45.

In some examples, the controller 100 can change setting of the reference condition by applying a weight to the reference condition based on the outside temperature and the operating state.

For example, depending on a weather or an amount of water, the setting of the reference condition can be changed by applying the weight to the reference condition.

More specifically, when a current weather corresponds to winter or the outside temperature corresponds to a temperature lower than a certain temperature, the controller 100 can apply a weight of ±A ° C. to the reference condition by reflecting a fact that the temperatures of the drum 20 and the duct assembly 30 are lowered so as to change the setting of the reference condition.

In some examples, the drying step (S40) can include a second circulation step (S43) in which the controller 100 rotates the circulation fan 43 at the preset second circulation speed V2.

For example, in the second circulation step (S43), the controller 100 can drive (rotate) the circulation fan 43 at a speed equal to or higher than 3500 rpm and equal to or lower than 4500 rpm while the compressor 45 is driven.

In some examples, in the drying step (S40), the controller 100 can be configured not to operate the steam supply 90 (S34).

That is, in the drying step (S40), the controller 100 can drive the drum 20, the circulation fan 43, and the compressor 45.

Therefore, according to the drying step (S40), by driving the compressor 45, the temperatures inside the drum 20 and the duct assembly 30 can be increased, and the temperatures of the compressor 45 and the condenser 42 can be increased, so that the evaporator 41 can be sterilized.

In some examples, the controller 100 can further include a second drainage step (S49) for the preset drainage time td before activating the blowing step (S50).

That is, in the second drain step (S49), the controller 100 can operate the drain pump 62 to move the condensate collected in the water collecting portion 60, and can operate the control valve 63 to allow the condensate to flow to the drain pipe 65. Consequently, the condensate can be transferred to the water storage tank 72.

In some examples, the drainage time td can be 50 seconds or longer and 70 seconds or shorter.

In the blowing step (S50), the controller 100 can sterilize the evaporator 41 based on a thermal equilibrium phenomenon by stopping the driving of the compressor 45 after the drying step (S40), and can blow hot air inside the drum 20 and the duct assembly 30 for a preset blowing time so as to evaporate the moisture remaining in the drum 20 and the duct assembly 30.

As an example, in the blowing step (S50), the controller 100 can sterilize the evaporator 41 for a time of 20 minutes or longer and 30 minutes or shorter, and evaporate the moisture remaining in the drum 20 and the duct assembly 30.

In the blowing step (S50), the controller 100 can rotate the drum motor 51 at the reference speed Wr input in advance (S51). For example, the controller 100 can continuously rotate the drum motor 51 while maintaining the rotation speed of the drum motor 51 at a speed equal to or higher than 3000 rpm and equal to or lower than 3300 rpm, thereby continuously rotating the drum 20 at the constant speed.

Therefore, the controller 100 can control the surface temperature of the heat exchange assembly 40 to rise to a temperature equal to or higher than the reference temperature for the sterilization by promoting the occurrence of the thermal equilibrium phenomenon on the air circulation flow path by driving the drum 20.

In some examples, in the blowing step (S50) of the present disclosure, the controller 100 can stop the driving of the compressor 45 so as to transfer the heat of the condenser 42 to the evaporator 41 using the thermal equilibrium phenomenon (S52).

Specifically, while the compressor 45 is driven and a heat pump cycle is maintained, each of the air circulation flow path composed of the drum 20 and the duct assembly 30 and the condenser 42 is maintained at a temperature equal to or higher than a certain temperature by the heat pump cycle. In some examples, when the driving of the compressor 45 is stopped, the temperature of each of the air circulation flow path and the condenser 42 is not able to be maintained as the heat pump cycle is stopped, and the heat of at least one of the air circulation flow path and the condenser 42 moves to the evaporator 41, and thus, the thermal equilibrium phenomenon occurs. That is, the temperature of each of the air circulation flow path and the condenser 42 is reduced and the surface temperature of the evaporator 41 rises, so that the surface temperature of the evaporator 41 can rise to a temperature equal to or higher than the reference temperature Ts for the sterilization.

In addition, in the blowing step (S50), the controller 100 can stop the driving of the compressor 45, and remove the moisture remaining in the drum 20 and the duct assembly 30 by utilizing heat remaining inside the drum 20 and the duct assembly 30.

In addition, in the blowing step (S50), in order to circulate the heated air inside the drum 20 and the duct assembly 30 so as to remove the moisture remaining in the drum 20 and the duct assembly 30, the controller 100 can rotate (drive) the circulation fan 43 while maintaining the rotation speed of the circulation fan 43 at the second circulation speed V2 (S53).

Therefore, the controller 100 can promote the occurrence of thermal equilibrium phenomenon on the air circulation flow path via the driving of the circulation fan 43 so as to control the surface temperature of the heat exchange assembly 40 to rise to a temperature equal to or higher than the reference temperature.

In some examples, in the blowing step (S50), the controller 100 can rotate the circulation fan 43 for the preset blowing time.

In some examples, the blowing time tc can be equal to or greater than the reference time tr (tc≥tr).

In addition, the reference time tr can refer to a time for the sterilization of the heat exchange assembly 40.

In particular, the reference time tr can be set based on the operating frequency of the compressor 45.

For example, the reference time can be set corresponding to a magnitude of the operating frequency before stopping the driving of the compressor 45.

Specifically, when the magnitude of the operating frequency F before stopping the driving of the compressor 45 is lower than a reference value, the reference time can be set long as much as a degree to which the operating frequency f is lower than the reference value. In addition, when the magnitude of the operating frequency F is higher than the reference value, the reference time can be set short as much as a degree to which the operating frequency f is higher than the reference value.

Accordingly, after stopping the driving of the compressor 45, the controller 100 can maintain the stopping of the driving of the compressor 45 based on the magnitude of the operating frequency F before stopping the driving of the compressor 45.

Accordingly, the controller 100 can complete the blowing step (S50) after the elapse of the reference time tr.

In some examples, because blowing step (S50) is a step to remove the moisture, in the blowing step (S50), the controller 100 can be configured not to operate (stop the operation of) the steam supply 90 (S54).

According to the blowing step (S50), the surface temperature of the heat exchange assembly 40 can be maintained at the temperature equal to or higher than the reference temperature Ts for the sterilization for the reference time tr or longer using the thermal equilibrium phenomenon, and the washing water that can remain in the heat exchange assembly 40 can be removed via wind, so that there is an effect of preventing the moisture from remaining in the heat exchange assembly 40.

Figure 8:
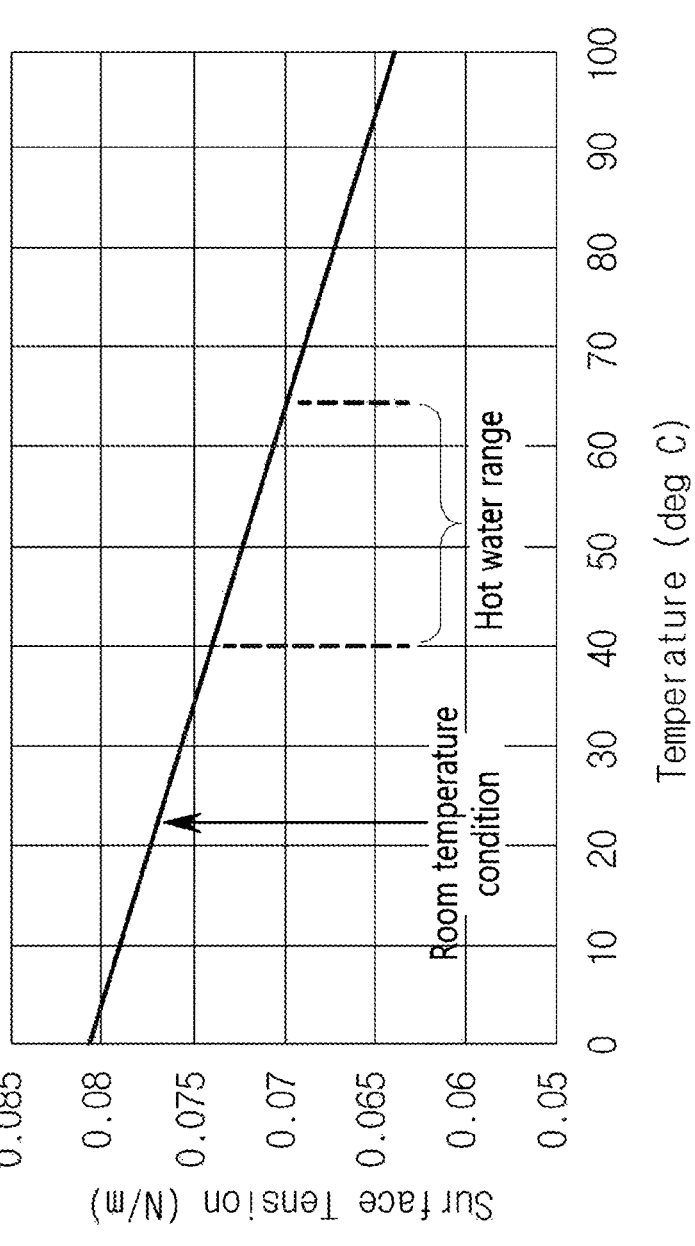
FIG. 8 is a graph showing an example of changes in surface tension of foreign substances and microorganisms based on a temperature in a method for controlling a laundry dryer.

In some examples, FIG. 7 discloses a graph showing changes in viscosity of foreign substances and microorganisms based on a temperature in a method for controlling a laundry dryer, FIG. 8 discloses a graph showing changes in surface tension of foreign substances and microorganisms based on a temperature in a method for controlling a laundry dryer, and FIG. 9 is a diagram for illustrating sterilization conditions according to a method for controlling a laundry dryer.

Referring to FIGS. 1 to 9, effects of the method for controlling the laundry dryer of the present disclosure will be described as follows.

First, an effect for each component of the present disclosure is as follows.

In the present disclosure, the drum 20 rotates from the steam supply step (S20) to the blowing step (S50) at the preset reference speed Wr (S21, S31, S41, and S51). Therefore, the drum 20 serves to prevent steam from being condensed on the surface of drum 20 when supplying steam, and to help the thermal equilibrium when stopping the driving of the compressor 45.

In the present disclosure, the compressor 45 is not driven when steam is supplied (S22), then is driven at the first compression frequency f1 in the washing step (S30) (S32), then is accelerated and driven at the second compression frequency f2 in the drying step (S40) (S42), and then is stopped and heats the evaporator 41 using the thermal equilibrium phenomenon in the blowing step (S50).

In the present disclosure, the circulation fan 43 is rotated at the first circulation speed V1 in the steam supply step (S20) and the washing step (S30) (S23 and S33), and is accelerated and rotated at the second circulation speed V2 in the drying step (S40) and the blowing step (S50) (S43 and S53). Therefore, the circulation fan 43 has the effect of drying and sterilizing the heat exchange assembly 40 by circulating hot steam and hot air.

In the present disclosure, the steam supply 90 is operated in the steam supply step (S20) (S24), and then stops operating (S34, S44, and S54).

In the present disclosure, the drain pump 62 is operated in the washing step (S35), the first drain step (S39), and the second drain step (S49) to supply the condensate as washing water, or to drain the condensate.

In the present disclosure, the control valve 63 can be controlled in the washing step to supply washing water to the heat exchange assembly 40.

Next, an effect for each step is as follows.

In the present disclosure, as steam is supplied toward the heat exchange assembly 40 in the steam supply step (S20), the surface tension and the viscosity of the foreign substances and the microorganisms attached to the surface of the heat exchange assembly 40 are reduced.

That is, as shown in FIGS. 7 and 8, when high-temperature steam is supplied to the heat exchange assembly 40 via the steam supply step (S20), the surface temperature of the heat exchange assembly 40 can rise, and the surface tension and the viscosity of the foreign substances and the microorganisms attached to the surface of the heat exchange assembly 40 can be reduced, so that the foreign substances and the microorganisms can be more easily removed from the heat exchange assembly 40.

In some examples, in the steam supply step (S20) of the present disclosure, the water stored in the steam generator 91 is sprayed three times in the steam spraying step (S24c). Therefore, there is an effect of preventing condensation of vapor inside the drum 20 due to excessive steam supply.

Next, the controller 100 of the present disclosure lowers the output of the circulation fan 43 and the compressor 45 in the washing step (S30) so as to enable stable power use even while driving the drain pump 62 and the control valve 63.

In addition, in the drying step (S40) and the blowing step (S50), there is an effect of sterilizing the evaporator 41 using the thermal equilibrium phenomenon by increasing the temperatures inside the drum 20 and the duct assembly 30 via controlling the driving of the compressor 45, and increasing the temperatures of the compressor 45 and the condenser 42.

That is, the controller 100 can effectively remove the bacteria present in the evaporator 41 by controlling the driving of the compressor 45 such that the sterilization operation for the evaporator 41 is maintained at a temperature equal to or higher than the reference temperature (60 degrees Celsius) for the reference time (10 minutes) or longer. The sterilization can refer to getting rid of or reducing bacteria or other living microorganisms.

In addition, there is an effect of improving the washing and sterilization effect of the heat exchange assembly 40 by removing the moisture that can remain in the heat exchange assembly 40 by the rotation of the circulation fan 43 in the blowing step (S50).

Hereinabove, the present disclosure has been described in detail through a specific implementation, but this is for specifically illustrating the present disclosure, and the present disclosure is not limited thereto. It is clear that the present disclosure can be modified or improved by a person having ordinary knowledge in the field within the technical spirit of the present disclosure.

All simple modifications or changes of the present disclosure fall within the scope of the present disclosure, and the specific protection scope of the present disclosure will be clarified by the appended claims.

The invention claimed is:

1. A laundry dryer comprising:
   a cabinet that defines an outer appearance of the laundry dryer;
   a drum rotatably located in the cabinet and configured to accommodate an object to be dried therein;
   a duct assembly configured to guide air discharged from the drum and to supply the air to the drum;
   a circulation fan configured to cause the air to move along the duct assembly;
   a heat exchange assembly disposed in the duct assembly and configured to exchange heat with the air in the duct assembly;
   a compressor configured to compress refrigerant to enable heat exchange between the refrigerant and the air in the duct assembly;
   a steam supply configured to generate steam and to supply the steam into the drum, the steam supply being configured not to directly supply steam to the heat exchange assembly;
   a washing device configured to spray washing water toward a surface of the heat exchange assembly;
   a sensor configured to sense a temperature of the heat exchange assembly; and a controller configured to control the drum, the circulation fan, the compressor, the steam supply, and the washing device, wherein the controller is configured to perform washing and sterilization operations by operating the steam supply and the circulation fan and then driving the compressor to thereby wash and sterilize the heat exchange assembly, wherein the controller is configured to, based on operating the steam supply, drive the circulation fan to transfer the steam inside the drum to the heat exchange assembly, and wherein the steam supply is configured to supply the steam into the drum without supplying steam directly to the heat exchange assembly such that the heat exchange assembly is configured to be sterilized by the steam that is supplied into the drum by the steam supply and subsequently transferred from the drum to the heat exchange assembly by operation of the circulation fan.

2. The laundry dryer of claim 1, wherein the controller is configured to rotate the drum based on operating the steam supply.

3. The laundry dryer of claim 1, wherein the controller is configured to (i) control the steam supply to spray steam for a preset spray time, (ii) then control the steam supply to stop spraying steam for a preset pause time, and (ii) then control the steam supply to respray steam for the preset spray time.

4. The laundry dryer of claim 1, wherein the controller is configured to rotate the circulation fan at a preset first circulation speed.

5. The laundry dryer of claim 1, wherein the washing device comprises:

a washing water sprayer configured to spray the washing water to the heat exchange assembly;

a drain pump configured to transfer condensate water stored in the cabinet; and a control valve configured to distribute the condensate water transferred by the drain pump toward the washing water sprayer, and wherein the controller is configured to, after terminating supply of the steam to the drum, control the washing device to spray the washing water to the heat exchange assembly based on a preset spray time and a preset pause time.

6. The laundry dryer of claim 5, wherein the controller is configured to drive the compressor at a preset first compression frequency based on starting an operation of the washing device.

7. The laundry dryer of claim 6, wherein the controller is configured to, after terminating the operation of the washing device, accelerate the compressor and drive the compressor at a preset second compression frequency.

8. The laundry dryer of claim 6, wherein the controller is configured to, after terminating the operation of the washing device, rotate the circulation fan at a preset second circulation speed.

9. The laundry dryer of claim 5, wherein the controller is configured to, after terminating supply of the steam to the drum, operate the drain pump for a washing time.

10. The laundry dryer of claim 1, wherein the controller is configured to perform the washing and sterilization operations without the object in the drum.

* * * * *